(12) United States Patent
Chawki

(10) Patent No.: US 9,968,760 B2
(45) Date of Patent: May 15, 2018

(54) DRESSING FOR FIXING AND PROTECTING A NEEDLE

(75) Inventor: Mokhtar Chawki, Le Vesinet (FR)

(73) Assignee: NEPHROKIT, Le Vesinet (FR)

( * ) Notice: Subject to any disclaimer, the term of this patent is extended or adjusted under 35 U.S.C. 154(b) by 248 days.

(21) Appl. No.: 13/001,560

(22) PCT Filed: Jun. 29, 2009

(86) PCT No.: PCT/FR2009/000803
§ 371 (c)(1),
(2), (4) Date: Jun. 24, 2011

(87) PCT Pub. No.: WO2009/156626
PCT Pub. Date: Dec. 30, 2009

(65) Prior Publication Data
US 2011/0245778 A1    Oct. 6, 2011

(30) Foreign Application Priority Data

Jun. 27, 2008 (FR) ...................................... 08 03629

(51) Int. Cl.
*A61M 25/02*    (2006.01)

(52) U.S. Cl.
CPC ..... *A61M 25/02* (2013.01); *A61M 2025/0253* (2013.01); *A61M 2025/0266* (2013.01)

(58) Field of Classification Search
CPC .... A61M 2025/0253; A61M 2025/026; A61M 2025/0266; A61M 2025/0273; A61M 2025/0246; A61M 25/02; A61M 2025/0206; A61M 2025/0213; A61M 2025/022; A61M 2025/0226; A61M 2005/1586; Y10S 128/06; Y10S 128/26

USPC .................................................. 604/174, 180
See application file for complete search history.

(56) References Cited

U.S. PATENT DOCUMENTS

| | | | | |
|---|---|---|---|---|
| 3,918,446 A | * | 11/1975 | Buttaravoli | 604/180 |
| 3,927,676 A | * | 12/1975 | Schultz | A61M 25/02 |
| | | | | 128/207.17 |
| 4,460,356 A | * | 7/1984 | Moseley | A61M 25/02 |
| | | | | 604/180 |
| 4,490,141 A | * | 12/1984 | Lacko et al. | 604/180 |
| 5,019,050 A | * | 5/1991 | Lynn | A61M 25/02 |
| | | | | 128/DIG. 15 |
| 5,038,778 A | * | 8/1991 | Lott | A61M 25/02 |
| | | | | 128/207.17 |

(Continued)

FOREIGN PATENT DOCUMENTS

| EP | 0284219 | * | 3/1988 |
|---|---|---|---|
| EP | 0 284 219 A2 | | 9/1988 |

OTHER PUBLICATIONS

International Search Report of PCT/FR2009/000803 dated Nov. 3, 2009.

*Primary Examiner* — Bhisma Mehta
*Assistant Examiner* — Laura Schell
(74) *Attorney, Agent, or Firm* — Sughrue Mion, PLLC

(57) ABSTRACT

Device for fixing and protecting a needle, this device having a first and a second adhesive part, separated by a central part, the first part being intended to be fixed to the skin, opposite the chosen penetration site for the needle, only one of the faces of the first part being adhesive, and a cutting line defining two longitudinal arms, each of these two arms including an outermost part belonging to the second adhesive part.

19 Claims, 5 Drawing Sheets

(56) References Cited

U.S. PATENT DOCUMENTS

| | | | | |
|---|---|---|---|---|
| 5,244,523 A | * | 9/1993 | Tollini | 156/227 |
| 5,546,938 A | | 8/1996 | McKenzie | |
| 6,267,115 B1 | * | 7/2001 | Marshel | A61M 25/02 |
| | | | | 128/877 |
| 6,722,369 B1 | * | 4/2004 | Kron | A61M 16/0488 |
| | | | | 128/207.17 |
| 7,618,400 B2 | * | 11/2009 | Chawki | 604/174 |
| 2008/0045905 A1 | * | 2/2008 | Chawki | 604/174 |

\* cited by examiner

DRESSING FOR FIXING AND PROTECTING A NEEDLE

CROSS REFERENCE TO RELATED APPLICATION

This application is a National Stage of International Application No. PCT/FR2009/000803 filed Jun. 29, 2009, claiming priority based on French Patent Application Nos. 08/03629, filed Jun. 27, 2008, the contents of all of which are incorporated herein by reference in their entirety.

The invention relates to the medical or veterinary field, and concerns the means for holding needles in place, more particularly, but not exclusively, wing needles.

The invention also concerns a device for protecting the site of entry of a needle.

The invention is of interest in particular with respect to the medical or veterinary use of intravenous catheters.

The invention finds an application in particular in the haemodialysis field, or the field of perfusions with needles/short intravenous catheters or devices of Cathlon® type (PTFE cannulas).

In other words, the invention relates to a device for fixing wing needles at the site of venous puncture, during a venous or arteriovenous perfusion, in particular for an arteriovenous fistula in haemodialysis.

It is common practice to withdraw or inject fluids (electrolytes, isotonic anaesthetic glucose saline, etc.) or to administer medicaments to a patient or an animal by means of a tube fixed to a needle or a catheter.

This needle or this catheter must be inserted manually and in a precise position, for example intravenously, intramuscularly or subcutaneously.

Wing needles are used for transfusions and taking blood samples, in particular. These needles take their name from the fact that they have a manual gripping zone in the shape of butterfly wings. The folding of these wings against one another enables a good grip and facilitates insertion of the needle under the skin. Once the needle has been put in place, the wings conventionally come to rest on the skin and an adhesive tape is placed on these wings and on the skin for the purpose of preventing extraction of the needle.

Examples of wing needles can be found in the US patents granted under the following numbers: U.S. Pat. Nos. 2,725,058, 3,064,648, 3,640,275, 4,194,504, 4,300,553, 4,627,842, 5,108,376, 5,149,328, 6,270,480.

When the needle is inserted into a blood vessel, even a slight movement of this needle can lead to a risk of phlebitis or of haematoma, the needle passing right through the vessel.

Conventionally, the needles are held in place by using a large quantity of pieces of adhesive tape. The quality of the holding of the needle in place therefore depends in particular on the care taken by the individual who puts these adhesive tapes in place. These adhesive tapes are uncomfortable and can cause skin problems.

The use of conventional adhesive tapes does not make it possible to avoid the risks of accidental extraction of the needles, for example during intravenous perfusions performed for children, who find it difficult to remain still for long periods.

The uncontrolled movements of individuals suffering from neurodegenerative diseases (Parkinson's, Alzheimer's) can also lead to the needles being torn off, with a loss of products essential to keeping the patient alive or to maintaining his or her physical or mental equilibrium, for example blood, curative products, nutritive elements, palliative care products.

The use of conventional adhesive tapes most of the time mask at least partly the tubing, such that it is sometimes difficult to visually check that the injection is taking place correctly or that fluids are draining correctly.

The periodic removal of the adhesive tapes in order to carry out this verification is laborious, unpleasant for the patient, and multiplies the risks of accidental movement of the needle.

It is common for these adhesive tapes to stick to the gloves of the handler, with the risks of being jabbed that are known and feared by nurses. The spreading of AIDS and of hepatitis, among other contagious diseases transmitted via the blood, has merely increased the fear of this risk. Now, conventional adhesives adhere to the wings of the needles and stick to the fingers of gloves, causing a tensile stress on the needle, the bevel of which may accidental jab the handler.

Rapid removal of the needle is sometimes desired and is not easy when this needle is fixed by a multitude of adhesive tapes placed any old how.

When the patient's skin is moist, subsequent to a stream of fluid or to perspiration, some of the adhesive tapes can detach from the skin, in such a way that the needle is no longer correctly fixed.

It is estimated that approximately 80% of hospitalized patients are subjected to a treatment administered via intravenous catheter. Although peripheral intravenous catheters are less subject to infection than deep intravenous catheters and central venous catheters, staphylococcal infections of peripheral venous catheters are not exceptional. Needle movements are presumed to promote these infections.

For some patients, peripheral catheters are used chronically. This is in particular the case of patients suffering from acute or chronic renal insufficiency and treated by haemodialysis, or extrarenal purification.

The haemodialysis session lasts approximately four hours, and must be carried out three times a week.

Three types of vascular access predominate for haemodialysis: arteriovenous fistulae AVFs, arteriovenous stents or grafts, and central venous catheters CVCs.

AVFs are anastomoses created surgically so as to connect an artery and a vein of the patient, commonly in the forearm, or the arm, most commonly between a radial or humeral artery and its homonymous vein. This anastomosis makes it possible to increase the blood flow within said vein. The creation of an AVF greatly modifies the appearance of the patient's forearm, by creating aneurysmal zones. This is the reason for which many rigid devices for holding needles in place, known in the prior art, cannot be used for holding dialysis needles in place on an AVF.

The needles used for puncturing AVFs are of large calibre, with an internal diameter typically ranging from 1.6 to 2 mm. The needle taking the patient's blood to the dialysis machine is called artery, that restoring the blood to the patient being called vein.

During a haemodialysis session on a patient, several incidents or accidents must be avoided.

Poor fixing of the needle represents a real danger to the patient, given the high operating flow rates of an AVF. Any haemorrhage from the point of puncture may prove to be fatal to the patient. Furthermore, during haemodialysis, an anticoagulant is used to limit the risks of clogging of catheter lumens due to thrombosis. Because of the high blood flow rates and the use of an anticoagulant, the risks associated with dialysis needles being accidentally pulled out are very high.

It is common to observe local bleeding between the cutaneous wall and the point of insertion of the needle, this being a factor for infectious contamination through the puncture wall. In order to avoid this pitfall, fixing devices must impose a permanent penetration pressure on the needle during dialysis.

During the puncture or in the course of a dialysis session, a needle may be transfixing. In other words, the needle may pass through the walls of the vessel and induce a haematoma. When it is the venous needle, the blood is reinjected under pressure during the dialysis session and creates a voluminous haematoma. More rarely, the needle penetrates the underlying artery, which causes a deep haematoma. An aneurysm may develop on the artery later on. Such an aneurysm requires surgical treatment. During dialysis, a haematoma may occur when the needle is fixed after having partially run through the vessel wall. This needle may become transfixing during an uncoordinated or unintentional movement by the patient. The dialysis session must then be prematurely interrupted, with the cost being a poor quality of extrarenal purification.

If the needle accidentally comes out while the extracorporeal circulation is functional, this is a serious accident. It is in particular very serious when it is the venous needle. Such an accident exposes the patient to the risk of death due to iatrogenic haemorrhage. If there is no specific alarm on the extracorporeal circulation, the blood pump continues to operate and drains the patient of his or her blood.

Such an accident is liable to occur, for example, in patients who are agitated, or depressive or epileptic, or suffering from chorea, or from a neurodegenerative disease such as Parkinson's disease or parkinsonian syndrome, or afflicted with convulsions for various reasons.

Unexpected disconnection of the arterial needle exposes the patient to bleeding at the point of puncture and to the risk of a gas embolism. Although rare due to the presence of an air detector in modern dialysis machines, this risk remains real when the blood flow rates are high, due to the latency in response of the safety clamp.

Simultaneous disconnecting of the two needles will have two consequences for the patient: despoilment of 250 cc of blood, and bleeding at the points of puncture. This bleeding will require interruption of the dialysis session and compression before possibly starting up a new session.

The stents or graft are put in place surgically, and also result in an arteriovenous link, provided by a canal made of biocompatible polymer material. The dialysis needles should be inserted into this synthetic canal, which requires quite a considerable manual effort.

The risks associated with the disconnecting of dialysis needles implanted in an AVF are substantially identical to those of disconnecting of the dialysis needles implanted in a graft.

Wing needles for haemodialysis are conventionally fixed with several adhesive tapes, at least one of which is stuck down in the form of a chevron or like a tie, by passing the adhesive under the tubing, and then over the wings.

Conventional devices for fixing perfusion catheters or needles cannot be used in most dialyses, for the following reasons.

First, a certain number of these prior devices are rigid. Now, AVF, the first-line vascular approach and which is the most widely used, leads to the appearance of aneurysmal zones, since the skin is very deformed in the region of the AVF. The use of rigid fixing devices causes repeated irritation of the skin, promoting excoriations which are very effective purveyors of bacterial contamination. Furthermore, the fistulae may be kept active for very many years, and the skin of certain dialysed patients is not very supple and is thin and fragile due to age.

Second, a certain number of prior devices for fixing needles comprise straps. Such straps are absolutely prohibited for patients carrying an AVF, due to the risk of garrotting that may lead to ischaemia.

Third, a large number of the prior devices for fixing needles are large in size. Now, AVFs are often short in length, such that the two, artery and vein needles must be placed close to one another.

Document EP 0 284 219 discloses a dressing for fixing a catheter or a cannula on the skin. The dressing is provided with a longitudinal separating line followed by an elongated hole for the passage of a cannula connector.

The dressing disclosed in EP 0 284 219 has many drawbacks. Its manufacturing is complex and expensive. In particular, this known dressing comprises a first peel-off strip, the end of which forms a gripping tongue, whereby this first peel-off strip is to be positioned when bent, between an adhesive mass and the end of a second peel-off strip. Applying and removing this known dressing is tricky. During the applying, the nurse has indeed to grab with both hands the dressing to remove both peel-off strips, thereby freeing the lower surface of the dressing, which surface is entirely adhesive. The risk is high, of unexpected gluing on the nurse's gloves during the applying or removal of the dressing.

Document U.S. Pat. No. 4,490,141 discloses a device for fixing a catheter. The device disclosed in this known document has many drawbacks. In particular, this device does not cover the puncture site and does not protect it from possible bacterial contamination. In addition, this known device does not allow for an efficient limitation of the risk of needle displacement.

After a thorough study of the problems presented above, the present inventor has designed a product which provides many advantages for largely reducing the difficulties mentioned.

In complete opposition to the conventional means of the prior art, in particular those described in the documents of patents U.S. Pat. No. 4,863,432, U.S. Pat. No. 4,534,762, U.S. Pat. No. 4,490,141 and U.S. Pat. No. 5,087,248, the present inventor proposes a device in which the needle, in particular a wing needle, is substantially not stuck to the skin, neither is it in contact with any adhesive tape, but remains, despite these choices which a priori go against nature, firmly in position.

According to a first subject, the invention relates to a device for fixing and protecting a needle, this device comprising a first and a second adhesive part, separated by a central part, the first part being intended to be fixed to the skin, advantageously opposite the chosen penetration site for the needle, only one of the faces of the first part being adhesive, this device comprising a cutting line defining two longitudinal arms, each of these two arms comprising an outermost part belonging to the second adhesive part.

Advantageously, the first part is adhesive on its front face, the second part being adhesive on its back face only.

Advantageously, the dressing is made of an elastic material, in particular elastic in the longitudinal and transverse directions. The dressing may thus follow the curvatures of its support, for example the curvatures of the body.

Advantageously, the dressing is made of transparent, translucent or semi-transparent material, at least with regard to its central part. Visual detection of any anomaly, in particular at the penetration point, is thus facilitated.

In one implementation, the dressing comprises a slit, which is in particular longitudinal, extending in its central part. This slit extends at least partly into the first adhesive part. The central part has a front face and a back face and no adhesive on the front face and no adhesive on the back face so that the central part is non-adhesive.

Advantageously, the second part is substantially identical to the first part in shape, for example, oval, square or rectangular. This thus makes the manufacture of the dressing economical.

According to a second aspect, the invention relates to a perfusion kit comprising a device as presented above and comprising at least one needle or similar means.

Other subjects and advantages of the invention will emerge in the course of the following description of currently preferred embodiments, which description will be given with reference to the attached drawings, in which.

The dressing 1 for fixing and protecting a needle represented in the attached figures will, in the interests of simplicity, be denoted by the term "dressing" in the description below.

In the following, the term "longitudinal" is employed with reference to a first elongation direction of the dressing, and the term "transverse" refers to a substantially perpendicular direction.

Figure 1:
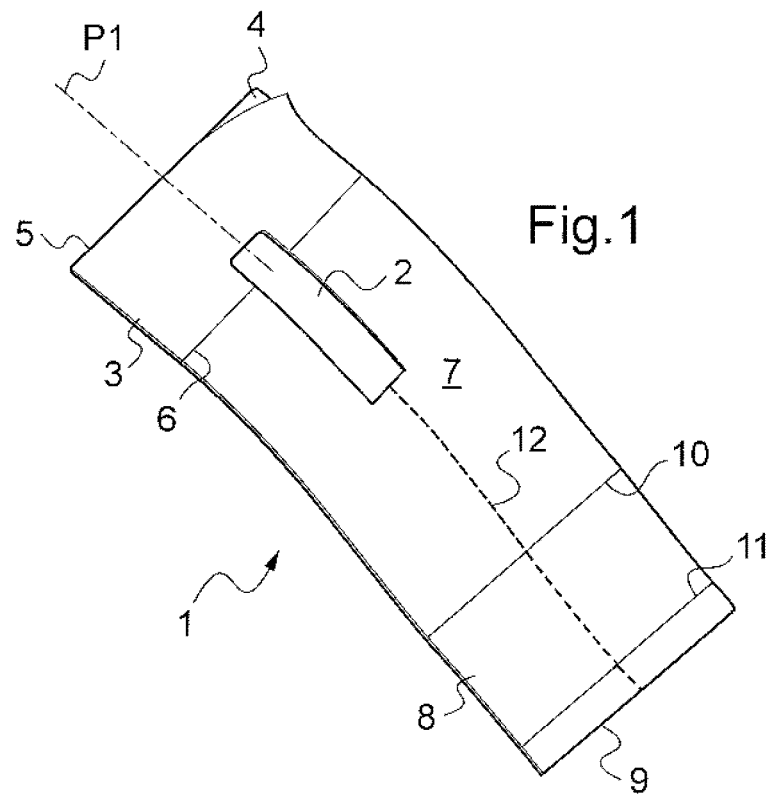
FIG. 1 is a plan view of a dressing for fixing and protecting a needle.

Reference is first made to FIG. 1.

The dressing 1 is generally in the shape of a slender strip.

In the embodiment represented, this slender strip is substantially rectangular and the dressing has a longitudinal plane of symmetry P1.

The dressing 1 comprises a longitudinal slit 2. As will emerge in the rest of this description, the dimensions of this longitudinal slit 2, and in particular its transverse dimension, are adapted to the dimensions of the puncture device, in particular to the diameter of a ferrule supporting a needle.

In the embodiment represented, this slit 2 is rectangular in shape. In other embodiments, not represented, this slit is oval, circular, square or polygonal.

In the embodiment represented, this slit 2 is midway across the width of the dressing. In other embodiments, not represented, this slit is off-centre and closer to one longitudinal edge of the dressing.

On a first part 3, referred to as front part, the dressing 1 is adhesive on its first face, referred to as lower face.

A peel-off strip 4 protects this adhesive lower front face, before the dressing is applied. This peel-off strip 4 advantageously comprises a gripping tongue. In one embodiment, the gripping tongue extends beyond the free transverse outermost edge 5 of the dressing 1.

In the embodiment represented, the adhesive lower front face extends transversely to the dressing and defines a substantially rectangular adhesive surface extending between the free transverse outermost edge 5 of the dressing 1 and a first transverse edge 6 of a central zone 7 of the dressing 1. In one embodiment, the gripping tongue of the peel-off strip slightly covers the central zone 7, beyond the first transverse edge 6.

In the depicted embodiment, the longitudinal slit 2 extends mainly in the central zone 7 of the dressing, and extends slightly beyond the first transverse edge 6 of the central zone 7. In other embodiments, not depicted, the longitudinal slit 2 extends up to the immediate vicinity of the free transverse outermost edge 6 but does not extend in the first part 3.

On a second part 8, referred to as back part, the dressing 1 is adhesive on its second face, referred to as upper face.

A peel-off strip protects this adhesive upper back face, before the dressing is applied. This peel-off strip 4 advantageously comprises a gripping tongue. In one embodiment, the gripping tongue slightly covers the central zone 7.

In the embodiment represented, the adhesive upper back face extends transversely to the dressing and defines a substantially rectangular adhesive surface extending between a free transverse outermost edge 9 of the dressing and a second transverse edge 10 of the central zone 7 of the dressing.

By virtue of the detachment lines 11, the peel-off strips or films protecting the adhesive surfaces can be removed according to precise planes. The fixing of the dressing is thus facilitated, without any risk of sticking to the gloves of the handler, or of gathering.

The dressing 1 is provided with a longitudinal cutting line 12.

In the embodiment represented, this cutting line starts from the transverse edge 9 and goes as far as the longitudinal slit 2.

In other embodiments, not represented, this cutting line does not go as far as the slit 2. Such an implementation is useful when the perfusion tubing is cylindrical and very flexible, with a risk of crushing.

The term "cutting line" denotes herein any line of slots, grooving, perforations, precut or thinning, the technique used to produce this line of lower resistance depending, as is known per se, on the type of material used for the dressing.

The term "cutting line" also denotes any trace on the dressing which guides the handler for cutting the dressing using a tool.

In an advantageous embodiment, the dressing is made of flexible polymer material or coated fabric, the line of lower resistance being a precut line. The term "flexible" denotes herein an ability to mould the curvatures of a surface where the dressing is applied, for example a forearm of a patient, this flexibility being ensured by the choice of the material and the thickness thereof. The term "flexible" also denotes herein an ability, for the material of the dressing, to support a certain amount of stretching.

The dressing is advantageously transparent, translucent or semi-transparent, in particular in its central zone 7.

As an example, dimensions of the dressing depicted in FIG. 1 are the following:
  a) for the first part 3, referred to as the front part, dimensions of the adhesive surface: 40 mm by 25 mm;
  b) for the second part 8, referred to as the back part, dimensions of the adhesive surface: 40 mm by 15 mm, distance between the free transverse edge 9 and the detachment line: 5 mm;
  c) for the central part 7, distance between the transverse edges 6, 10: 60 mm, width of the central part: 40 mm;
  d) for the longitudinal slit 2: width 7 mm, length 27 mm;
  e) for the peel-off strips: width of the tongues: 4 mm.

Figure 2:
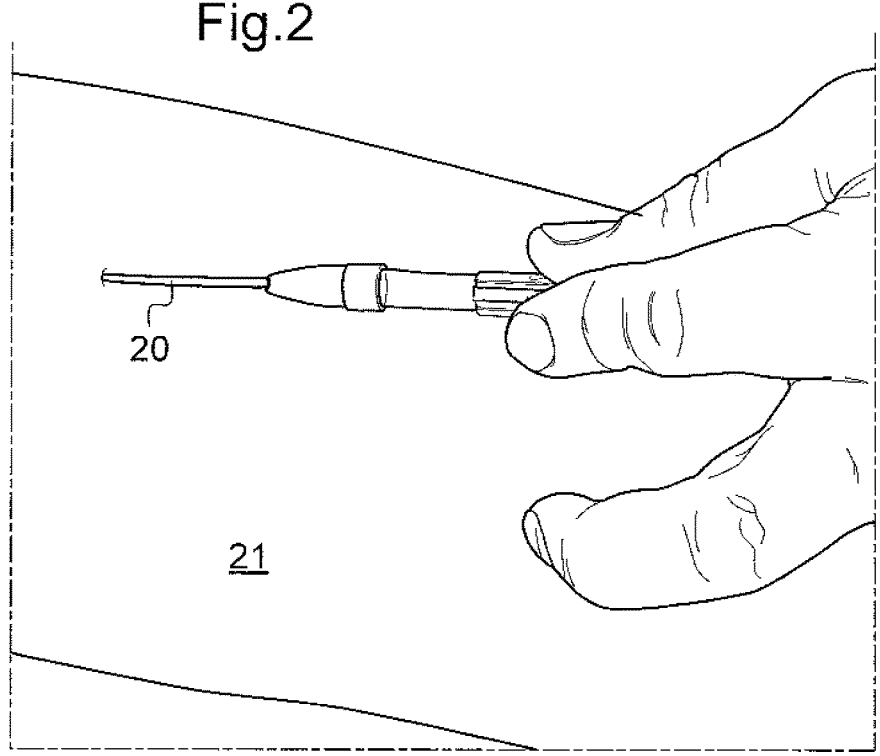
FIGS. 2 to 7 are schematic perspective views illustrating the placement of a dressing as represented in FIG. 1, for a needle introduced, for example, into the forearm of a patient.

Reference is now made to FIG. 2 et seq. which illustrate putting the dressing in place.

In a first step, represented in FIG. 2, a needle 20, for example a perfusion needle, is inserted, for example into the forearm 21 of a patient. This introduction of the needle is conventional. This needle may be that of a Cathlon®, or alternatively a wing needle. The needle is, for example, introduced into a blood vessel or into an AVF.

The handler then removes the peel-strip 4 covering the adhesive lower front face of the dressing.

The handler fixes this lower front face against the patient's skin.

Figure 3:
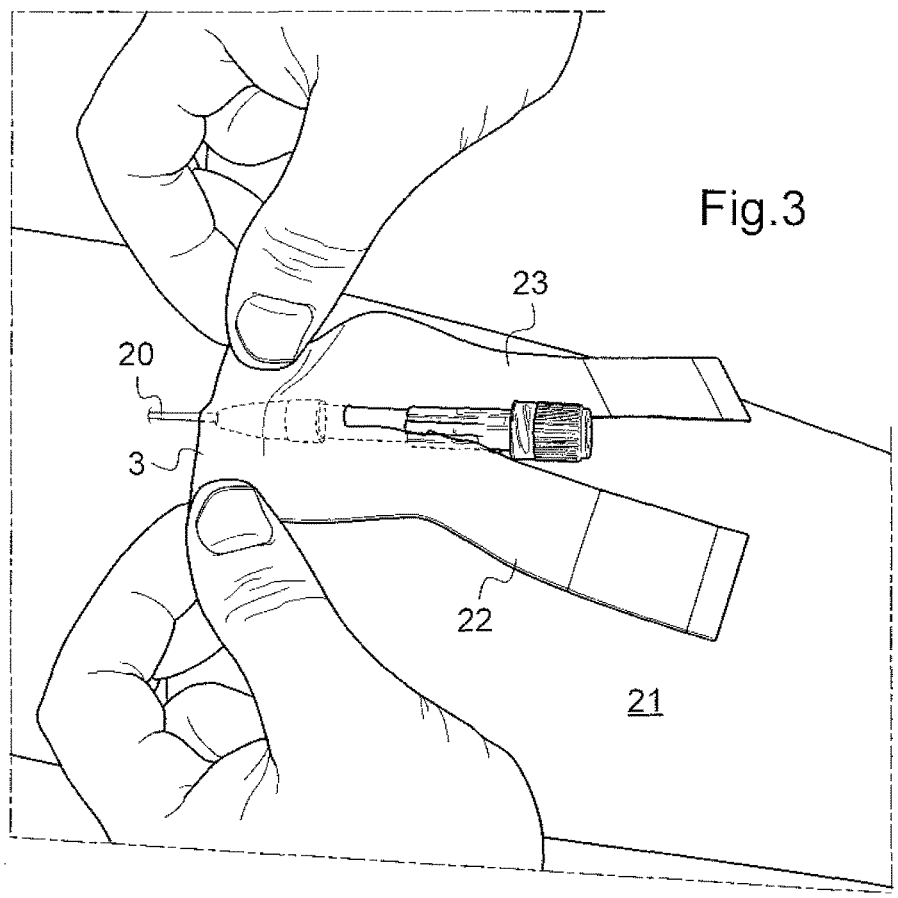

As is represented in FIG. 3, the adhesive lower front face of the dressing 1 then takes up a position on either side of the needle and covers this needle over a small distance, of the order of a few millimeters.

The handler has separated or separates the two arms 22, 23 of the dressing 1, if necessary by cutting this dressing along the line of lower resistance 12.

The longitudinal slit 2 makes it possible to move the two arms 22, 23 of the dressing 1 apart, taking into account the volume of the end of the tubing.

Figure 4:
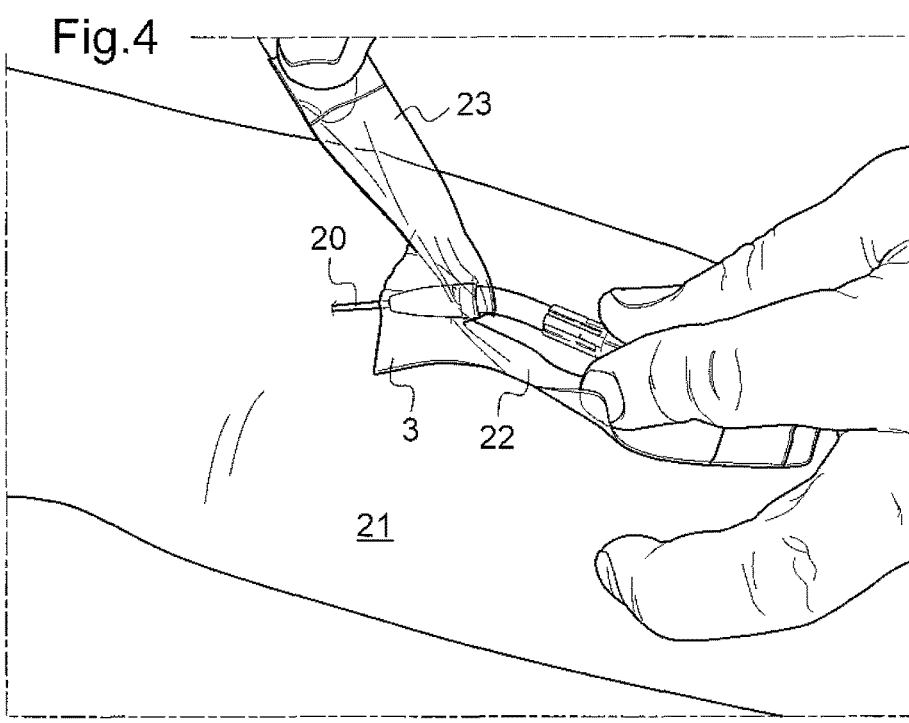

The handler takes hold of a first arm 23 of the dressing, located to the right of the needle, and passes this arm under the tubing, so as to then fold it back over the tubing (FIG. 4). Since the peel-off strip protecting the adhesive upper face of the dressing is still in place, the arm 23 does not stick to the handler's fingers.

The handler fixes the first arm 23 of the dressing to the skin of the patient.

Figure 5:
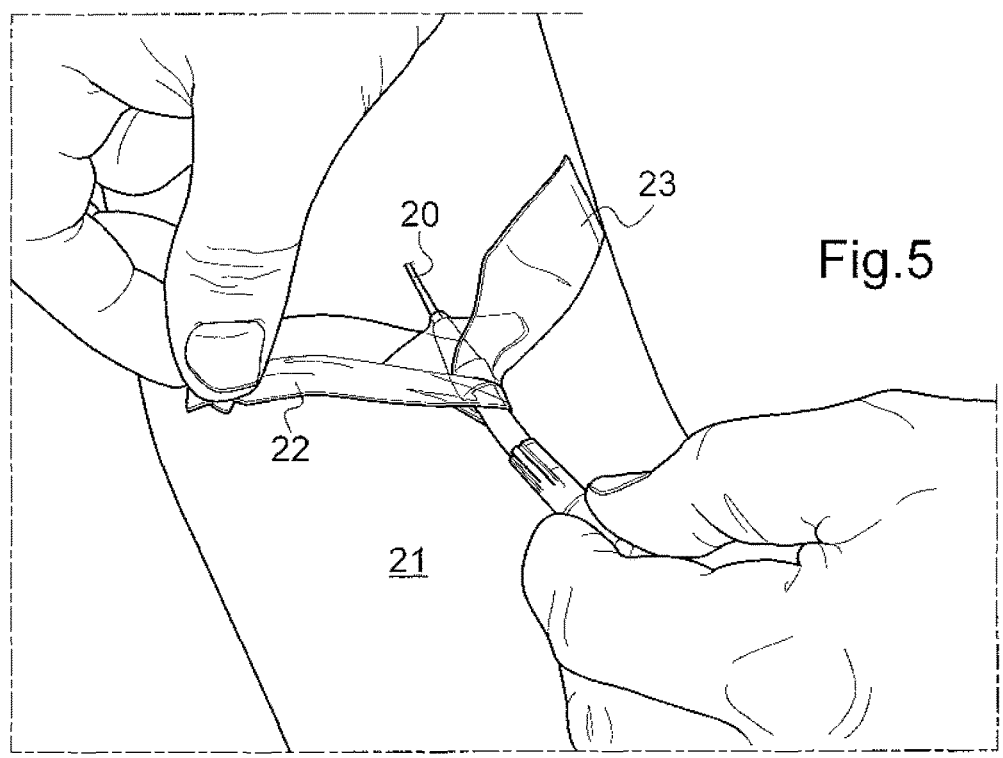
Figure 6:
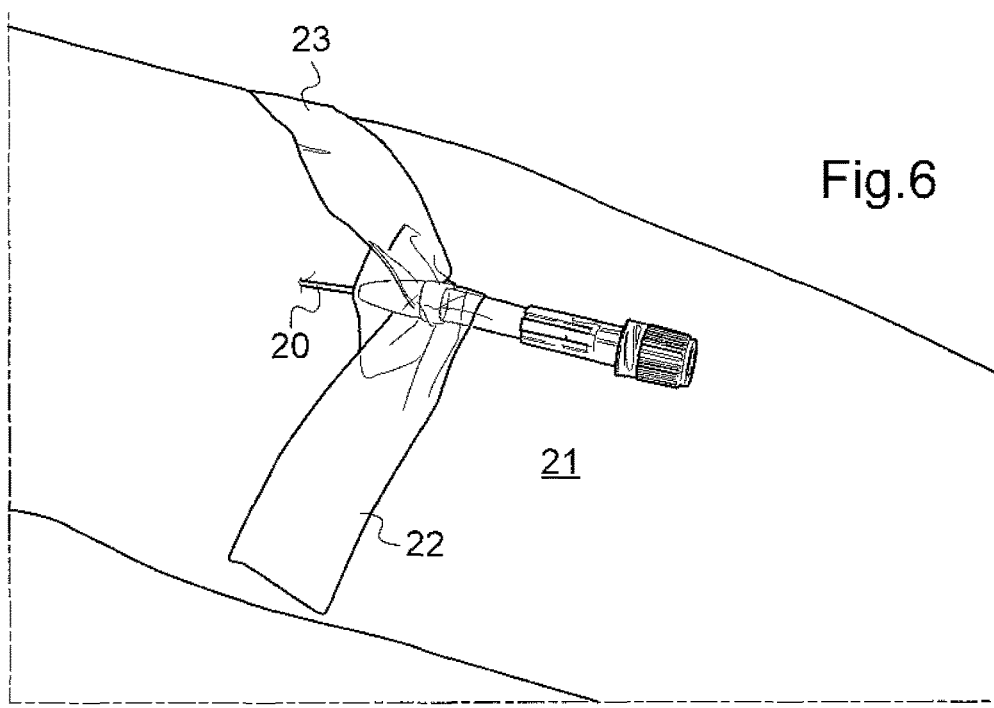
Figure 7:
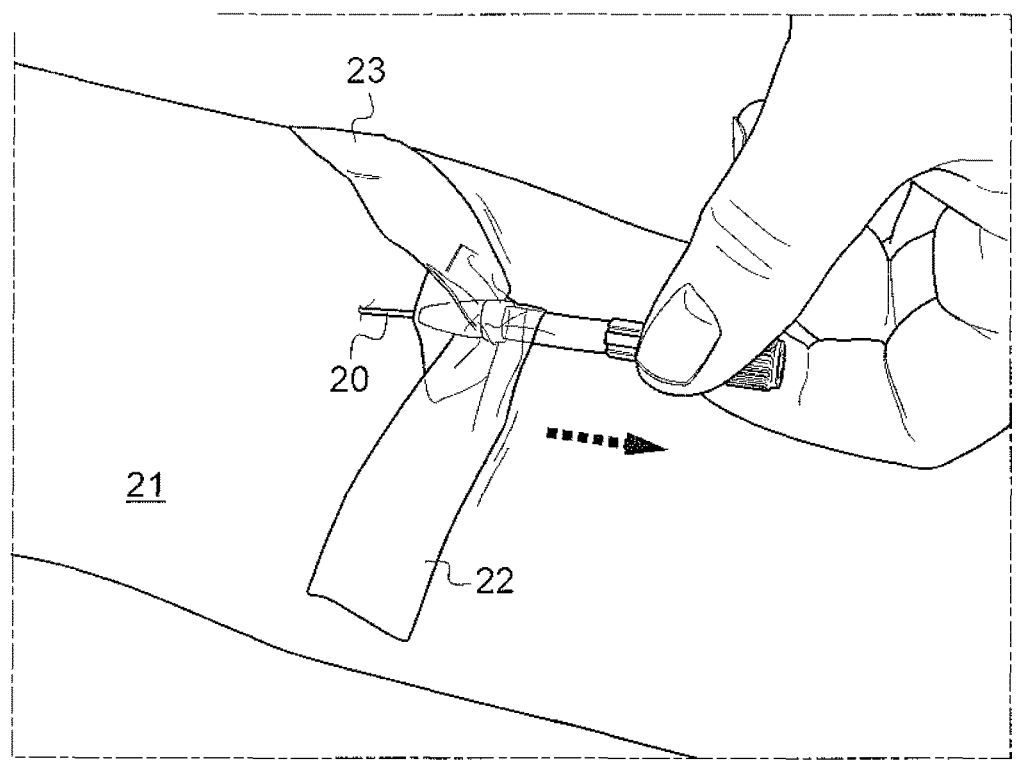

The handler then takes hold of the second arm 22 of the dressing, located to the left of the needle, and passes this arm under the tubing, so as to then fold it back over the tubing (FIG. 5). Since the peel-off strip protecting the adhesive upper face of the dressing is still in place, the arm 22 does not stick to the handler's fingers.

The handler fixes the second arm 22 of the dressing to the skin of the patient.

It should be noted that the handler may use a wing needle, folding the wings back so as to have a better grip on the needle and to direct it more easily, and releasing the wings when the needle has been put in place, the wings then coming to rest against the front face of the dressing 1, on either side of the slit 2. The width of the slit 2 is then substantially less than the width of the wings, when these wings are in the released position.

Where appropriate, the longitudinal reinforcement strips are placed on either side of the slit 2.

The invention does not require the handler to change his or her habits as regards the introduction of the needle through the skin, which is very reassuring for the latter.

The flexibility of the dressing makes it possible to follow the contours of the skin, including in the region of the aneurysmal zones of AVFs. Advantageously, the material constituting the arms 22, 23 and, where appropriate, the entire dressing 1 is extensible in at least one, longitudinal direction, and even more advantageously in both directions, longitudinal and transverse. The dressing is thus even more adaptable to the various curvatures of the patient's body.

It should be noted that the needle, in particular the wings on the wing needle, are no longer stuck to the skin, nor are they in contact with an adhesive zone. Only the outermost part of the arms 22, 23 is adhesive. The removal of the needle is thus made safer than in the prior devices. It is in fact sufficient to detach the arms 22, 23, which are stuck down at a distance from the needle, and then to detach the front part of the dressing, this front part covering the needle only over a small surface.

The dressing makes it possible to visualize the puncture site and to detect any anomaly that may occur.

Figure 8:
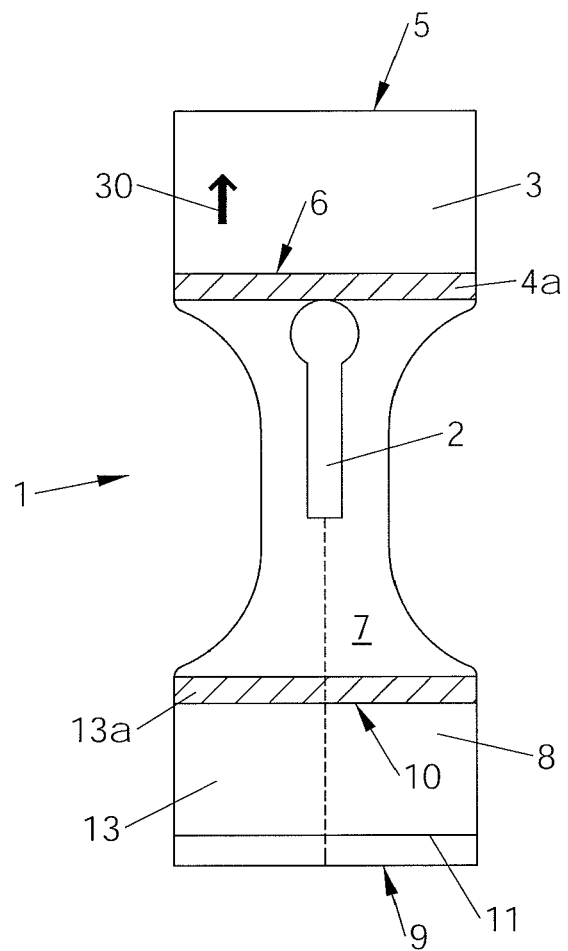
FIG. 8 is a planar view of a dressing for fixing and protecting a needle, according to an alternate embodiment.

Reference is now made to FIG. 8 which depicts different particular embodiments.

In order to simplify, all those embodiments are included within one single figure. However, it shall be noted that each of those embodiments may be used in a dressing of the type previously disclosed with reference to FIGS. 1-7.

In a first particular embodiment, the longitudinal slit 2 advantageously has a key hole shape, such design facilitating the gripping of the needle ferrule.

In yet a second embodiment, an indicator, such as an arrow 30, indicates the direction for applying the dressing.

In a third particular embodiment, the central part 7 is of low width, whereby such a design facilitates the positioning of the arms during the applying of the dressing.

In yet a fourth specific embodiment, gripping tongues 4a, 13a of the peel-off strips 4, 13 are provided with a mark, e.g. they are coloured in order to facilitate their positioning and use.

In a fifth specific embodiment, a medicine is mixed within the adhesive mass.

In yet another specific embodiment, the material of the dressing is provided with micro perforations.

The invention claimed is:

1. A device for fixing and protecting a needle, comprising:
a first adhesive part and a second adhesive part, separated by a central part,
the first adhesive part being intended to adhere to the skin, near a chosen penetration site for the needle, the first adhesive part having a front face and a back face, only the front face of the first adhesive part being adhesive,
the second adhesive part having a front face and a back face, only one face of the second adhesive part being adhesive, the second part containing adhesive on the back face so as to face in a direction opposite the adhesive on the first adhesive part;
the central part having a front face and a back face and no adhesive on the front face and no adhesive on the back face so that the central part being non-adhesive, a longitudinal slit extending in the central part;
a longitudinal line of lower resistance extending along a longitudinal direction of the device to permit separation along the longitudinal line and defining two longitudinal arms, each of these two arms extending further longitudinally than transversally and comprising an outermost part belonging to the second adhesive part, the longitudinal line of lower resistance starting from a transverse edge of the second adhesive part and going as far as the longitudinal slit.

2. The device according to claim 1, made of an elastic material.

3. The device according to claim 1, made of transparent, translucent or semi-transparent material, at least with regard to the central part.

4. The device according to claim 1, wherein the slit extends at least partly into the first adhesive part.

5. The device according to claim 1, wherein the second part is substantially identical to the first part in shape.

6. The device according to claim 1, wherein the second part is substantially identical to the first part in shape and is oval, square or rectangular.

7. The device according to claim 1 made of an elastic material that is elastic in the longitudinal and transverse directions.

8. The device according to claim 1, wherein the first adhesive part and the second adhesive part are spaced apart longitudinally.

9. The device according to claim 1 wherein each of the front face of the first adhesive part and the back face of the second adhesive part have a peel-off strip.

10. The device according to claim 1, wherein the two longitudinal arms are releasably coupled along the longitudinal line of lower resistance.

11. The device according to claim 1, wherein the longitudinal line of lower resistance does not extend through the first adhesive part.

12. The device according to claim 1, wherein the line of lower resistance is one of a slot, groove, perforation, precut, or thinning of a material of the device to permit the separation along the longitudinal line.

13. The device according to claim 1, wherein each of the two arms have a length in the longitudinal direction greater than a length of the first adhesive part in the longitudinal direction.

14. The device according to claim 1, wherein the longitudinal slit has a key hole shape.

15. The device according to claim 1, wherein the two arms extend on both sides of the longitudinal line of lower resistance further longitudinally than transversally.

16. A perfusion kit comprising:
a needle and a device for fixing and protecting said needle, the device comprising:
a first adhesive part and a second adhesive part, separated by a central part,
the first part being intended to be fixed to the skin, near a chosen penetration site for the needle, the first adhesive part having a front face and a back face, only the front face of the first part being adhesive,
the central part having a front face and a back face and no adhesive on the front face and no adhesive on the back face so that the central part being non-adhesive, a longitudinal slit extending in the central part;
the second adhesive part having a front face and a back face, only one face of the second adhesive part being adhesive, the second part containing adhesive on the back face so as to face in a direction opposite the adhesive on the first adhesive part; and
a longitudinal line of lower resistance to permit separation along the longitudinal line and defining two longitudinal arms, each of these two arms extending on both sides of the longitudinal line further longitudinally than transversally and comprising an outermost part belonging to the second adhesive part, the longitudinal line of lower resistance starting from a transverse edge of the second adhesive part and going as far as the longitudinal slit.

17. A device for fixing and protecting a needle, comprising:
an elongated flexible material extending along a longitudinal axis, the flexible material comprising a first part at one end, a second part at another end extending further longitudinally than transversally and a third part between the first part and the second part, the first part configured to adhere to the skin near a chosen penetration site for the needle;
the first part has a front face and a back face and an adhesive on the front face;
the second part has a front face and a back face, the second part containing adhesive on the back face so as to face in a direction opposite the adhesive on the first adhesive part;
the third part has a front face and a back face and no adhesive on the front face and no adhesive on the back face, a longitudinal slit extends in the third part; and
the second part comprising a line of lower resistance extending along the longitudinal axis permitting separation of the second part into two arms, the line of lower resistance starting from a transverse edge of the second part and going as far as the longitudinal slit.

18. The device according to claim 17, wherein the line of lower resistance extends into the third part, thereby continuing the two arms into the third part.

19. The device according to claim 17, wherein the line of lower resistance extends into the third part, thereby continuing the two arms into the third part with adhesive at distal ends of the two arms.

* * * * *